US008346331B2

(12) United States Patent
Bunce et al.

(10) Patent No.: US 8,346,331 B2
(45) Date of Patent: Jan. 1, 2013

(54) DECEPTION DETECTION AND QUERY METHODOLOGY FOR DETERMINING DECEPTION VIA NEUROIMAGING

(75) Inventors: Scott C. Bunce, Philadelphia, PA (US); Ajit Devaraj, Philadelphia, PA (US); Meltem Alkan Izzetoglu, Drexel Hill, PA (US); Banu Onaral, Philadelphia, PA (US); Kurtulus Izzetoglu, Drexel Hill, PA (US); Kambiz Pourrezaei, Philadelphia, PA (US)

(73) Assignees: Drexel University, Philadelphia, PA (US); Philadelphia Health & Education Corporation, Philadelphia, PA (US)

( * ) Notice: Subject to any disclaimer, the term of this patent is extended or adjusted under 35 U.S.C. 154(b) by 1270 days.

(21) Appl. No.: 12/105,979

(22) Filed: Apr. 18, 2008

(65) Prior Publication Data
US 2008/0306365 A1 Dec. 11, 2008

Related U.S. Application Data

(63) Continuation-in-part of application No. PCT/US2006/040847, filed on Oct. 18, 2006.

(60) Provisional application No. 60/727,616, filed on Oct. 18, 2005.

(51) Int. Cl.
*A61B 5/1455* (2006.01)
*A61B 5/04* (2006.01)

(52) U.S. Cl. .................. 600/323; 600/473; 600/544

(58) Field of Classification Search .................. 600/310, 600/322, 323, 340, 473, 544; 434/236
See application file for complete search history.

(56) References Cited

U.S. PATENT DOCUMENTS

| 6,240,309 | B1 * | 5/2001 | Yamashita et al. ............ 600/473 |
| 2004/0082862 | A1 | 4/2004 | Chance |
| 2006/0058683 | A1 | 3/2006 | Chance |

OTHER PUBLICATIONS

Bunce, S.C. et al., "Detecting deception in the brain: a functional near-infrared spectroscopy study of neural correlates of intentional deception," Proceeding of SPIE, vol. 5769, May 9, 2005, pp. 24-32.
Izzetoglu, K. et al., "NIR Spectroscopy Measurements of Cognitive Load Elicited by GKT and Target Categorization," Proceedings of the 36th Annual Hawaii International Conference on System Sciences on Jan. 6-9, 2003, Piscataway, MJ, USA, IEEE, Jan. 6, 2003, pp. 129-134.

* cited by examiner

*Primary Examiner* — Eric Winakur
(74) *Attorney, Agent, or Firm* — Woodcock Washburn, LLP

(57) ABSTRACT

Functional near-infrared (fNIR) neuroimaging is used to assess credibility, detect deception, and implement a query methodology for determining deception via neuroimaging. Oxygenation levels of portions of the brain are imaged via fNIR spectroscopy and utilized to determine if the subject is telling a lie or a truth. In an example configuration, oxygenation levels in the inferior and/or middle prefrontal cortical areas of the brain, such as the bilateral dorsolateral prefrontal and/or inferior frontal cortex, are measured to determine if a subject is lying relative to telling the truth. An example system includes a portable, flexible, belt like sensing device that is positioned proximate the subjects scalp. Sensed neural activity is transmitted either through wired or wireless means, to a processor for analysis of the sensed neural activity. The query methodology utilizes an attestation assertion that mitigates variance in brain responses due to the length or form of a question.

25 Claims, 12 Drawing Sheets

DECEPTION DETECTION AND QUERY METHODOLOGY FOR DETERMINING DECEPTION VIA NEUROIMAGING

CROSS REFERENCE TO RELATED APPLICATIONS

The present application is a continuation in part of International Patent Application Number PCT/US2006/040847, filed Oct. 18, 2006, which claims priority to U.S. Provisional Application No. 60/727,616, filed Oct. 18, 2005, entitled "DECEPTION DETECTION USING FUNCTIONAL NEAR-INFRARED SPECTROSCOPY," both of which are hereby incorporated by reference in their entirety.

STATEMENT REGARDING FEDERALLY-SPONSORED RESEARCH AND DEVELOPMENT

The invention was made with United States Government support under contract no. N00014-04-1-0119 awarded by the Office of Naval Research and Department of Homeland Security. The United States Government has certain rights in the invention.

TECHNICAL FIELD

The technical field relates generally to the detection of deception, and more specifically to detection of deception employing functional near-infrared spectroscopy. Additionally, the technical field relates generally to credibility assessment, or the inference of deception, and more specifically to credibility assessment employing functional near-infrared spectroscopy, as well as other neurophysiologic and brain imaging technologies. The technical field additionally relates generally to the detection of malingering, i.e., the faking of a symptom, employing functional near-infrared spectroscopy, as well as other neurophysiologic and brain imaging technologies.

BACKGROUND

A disadvantage of conventional polygraphy is the inferential nature of its methods. The sympathetic nervous system responses that are measured by the polygraph are not specific to deception. Conventional polygraphy for the detection of deception relies on psychophysiological measures of the sympathetic nervous system response, such as respiration rate, heart rate, and electrodermal activity, to detect anxiety associated with guilt or lying. These autonomic responses are common to any number of emotional, as well as cognitive and physiological responses. Because these psychophysiological responses are not specific to deception, the polygrapher does not actually measure deception per se. Rather, the polygrapher must infer deception based on differential psychophysiological responses to well-designed questions. Thus, conventional polygraphy suffers from a lack of specificity in differentiating guilt from fear or anxiety, and even anger, which can contribute to an unacceptably high level of false positives. Further, conventional polygraphy is subject to various inherent sources of variability, such as personality factors relating to the examiner and examinee, the question format, and the decision rules, for example.

Further, the relatively quick habituation of the autonomic measures used in conventional polygraphy, as well as the pain that results from extended occlusion of the blood supply by the blood pressure cuff, prevent the repetition of critical (e.g., the questions to which the examinee might be expected to lie) and comparison or control questions. As a result, in conventional polygraphy, the number of times critical questions can be repeated is limited (e.g., three times) because the ability to accurately infer a deceptive response diminishes with repetition.

Due to the lack of acceptable reliability, and specificity in particular, of conventional polygraphy, recent efforts to increase the reliability of credibility assessment have turned to more direct measures of central nervous system function during credibility assessment. Rather than assessing the psychophysiological correlates of guilt, anxiety, or even pleasure associated with deception, e.g., the emotional response to lying or to the fear of being caught, neuroimaging has been utilized to assess the neural pathways that underlie the cognitive as well as the emotional aspects of deception. In one known neuroimaging technique, encephalography, or EEG, voltage oscillations that reflect the neural activity associated with various cognitive and emotional events are measured. A disadvantage of measuring these voltage oscillations is that the relative spatial resolution is poor. Further, high-density electrode arrays are typically needed to localize activation sources.

Although central nervous system function has the potential to be more accurate than conventional polygraphy, it is widely held that there is no specific "deception circuit" in the brain, i.e., a set of neurons that are only activated when being deceptive, and not activated under any other circumstance.

Other attempts to identify the neural underpinnings of conscious deception comprise functional magnetic resonance imaging. Functional magnetic resonance imaging, however, is expensive, highly sensitive to motion artifacts, and confines participants to restricted positions. Also, U.S. Patent Application Publication No. 2006/0058683, which is a continuation in part of U.S. patent application Ser. No. 10/618,579 suggests an optical system for the detection of deceit.

SUMMARY

A safe, inexpensive, and readily deployable (e.g., field deployable) brain-imaging technology for use in detecting deception utilizes functional near-infrared (fNIR) spectroscopy. FNIR spectroscopy is utilized to detect increased activation of parts of the brain that are activated when a person is lying relative to telling the truth, and decreased activation in parts of the brain that are deactivated when a person is lying relative to telling the truth. A fNIR sensing device is placed proximate to a subject's head, and near-infrared light from the sensor is directed onto the subject's scalp. The infrared light passes though the scalp, skull, and brain tissue, where it is either absorbed by tissues in the blood, or reflected back to the surface of the scalp in a characteristic banana-shaped pathway. Absorption by specific tissues in the blood are indicative of neural activity associate with the subject's responses, and results in decreases in the amount of infrared light returning to the surface of the scalp, which is detected by the fNIR sensing device. In an example embodiment, the detected light is converted to an electrical signal and transmitted to a processor for analysis. Results of the analysis are rendered and indications of deception are provided. Results are available after post-test processing, or in real time, while the subject is being tested.

An example deception detection fNIR spectroscopic system comprises a flexible belt like array of sensors providing both sources of and detectors of NIR radiation, a transducer for converting the detected NIR energy (photons) to electrical energy (an electronic signal), a processor for analyzing the electrical energy, and a display device for rendering analysis results.

A method of questioning and measurement utilizing fNIR spectroscopy comprises the determination of a comparative baseline, multiple repetitions of critical questions, and the use of a particular type of query, referred to as an "attestation affirmation". Use of an attestation affirmation increases reliability in making a determination of deception or truthfulness. Neuroimaging modalities allow the capacity to repeat questions without habituation of the neural response, and without producing physical discomfort for the examinee. As such, the utilization of a comparative attestation affirmation, e.g., an indication of a query as to the truthfulness of a previous question is possible.

The attestation affirmation can be in the form of an audio or visual cue. For example, as an audio cue, the attestation affirmation can be a question of the general form "Was your answer to the previous question completely truthful?" Also, as an audio cue, the attestation affirmation can be in the form of any sound that is indicative of the question (e.g., a beep or the like). As a visual cue, the attestation affirmation can be a visual representation of the question on a display, an icon on a display, a light, or the like. Utilization of an attestation affirmation minimizes or eliminates variance in brain responses that might be due to the length or form of a critical question, or the specific affective response to any given critical question. The attestation affirmation allows the direct comparison of brain responses to identical questions with a YES or NO answer format, with the distinction between a truthful response and a false response being the examinee's knowledge about how she or he answered the former question. In an example embodiment, the attestation assertion is used multiple times during the determination of the comparative baseline period and during the formal questioning period.

In addition, the use of the visual presentation of a question with which the examinee has been well familiarized, thereby allowing relatively instantaneous recognition of the question, allows precise time-locks for averaging the brain response across multiple questions.

BRIEF DESCRIPTION OF THE DRAWINGS

The foregoing summary, as well as the following detailed description, is better understood when read in conjunction with the appended drawings. For the purpose of illustrating deception detection and query methodology for determining deception via neuroimaging, there is shown in the drawings exemplary constructions thereof, however, deception detection utilizing functional near-infrared spectroscopy is not limited to the specific methods and instrumentalities disclosed.

DETAILED DESCRIPTION OF THE ILLUSTRATIVE EMBODIMENT(S)

Figure 1:
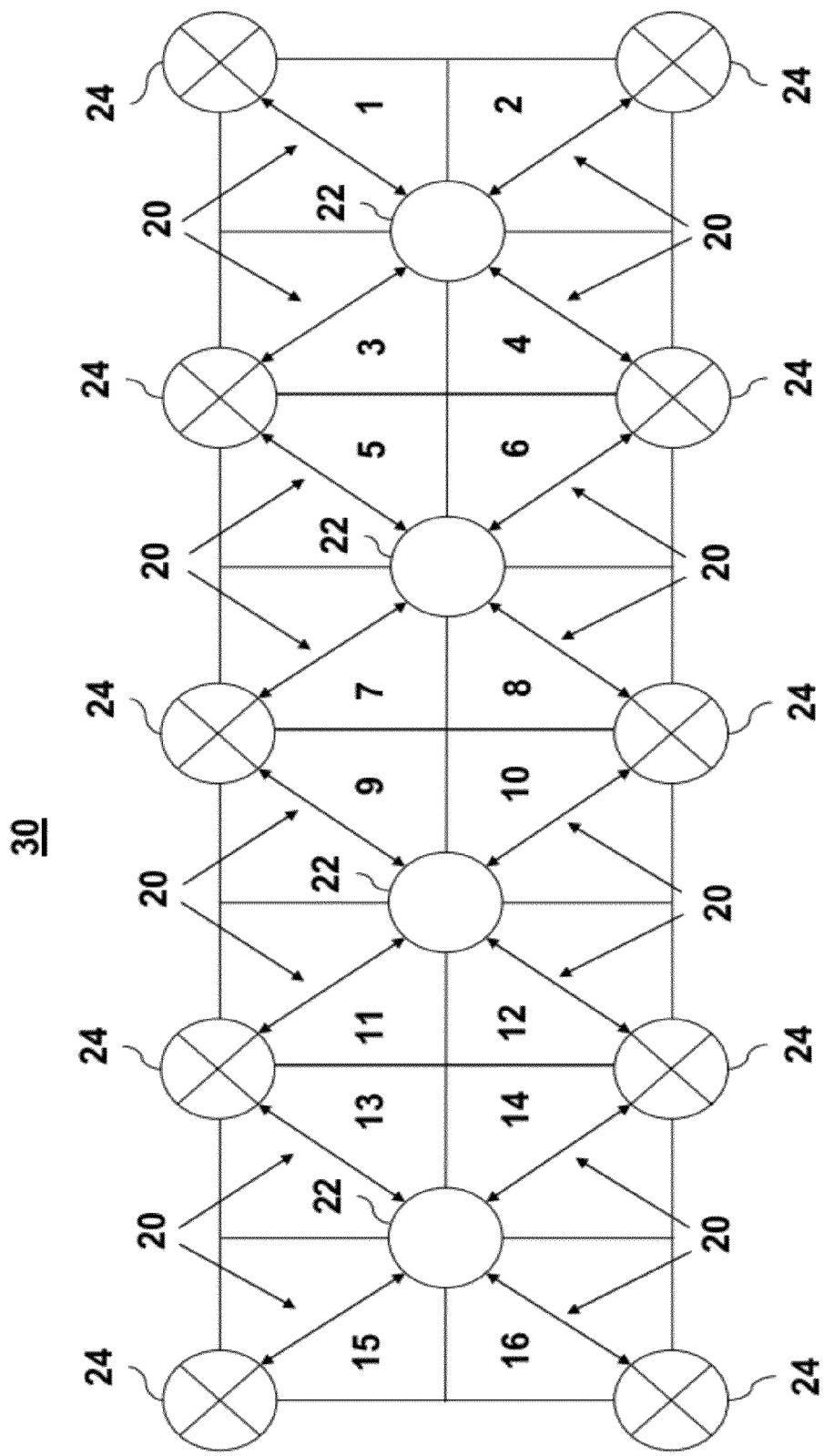
FIG. 1 is a schematic diagram of an example functional near-infrared sensing device 30 for deception detection.

Functional near-infrared (fNIR) spectroscopy is utilized to provide a safe, inexpensive, portable, and readily deployable brain-imaging technology for detecting deception and/or establishing credibility. The detection of deception includes the detection of malingering, such as faking an illness or symptom, faking an incapacity to remember, or feigning a memory problem by deliberately performing poorly on memory tasks. FNIR spectroscopy measures neuronal activity in the brain based on the relationship between metabolic activity and the oxygen levels in blood vessels. Knowledge that one is purposefully being misleading or lying can cause local fluctuations in blood oxygenation in the cortex. These local fluctuations of blood oxygenation are exploited to detect deception. In an example embodiment, neural pathways in the cortex of a brain are imaged and analyzed to detect deception. Specific wavelengths in the near-infrared spectrum (e.g., 700 to 900 nanometers) of light are introduced at the scalp to enable the noninvasive measurement of hemodynamic changes in the concentration of deoxygenated hemoglobin (deoxy-Hb) and oxygenated hemoglobin (oxy-Hb) during brain activity.

Photons entering biological tissue interact with the tissue in several ways, including absorption and scattering, among others. Scattering occurs at an unchanged frequency when the tissue is stationary. In the case of moving particles in the tissue (e.g., blood cells), the scattering can be accompanied by a Doppler shift. Most biological tissues are relatively transparent to light in the near-infrared range between 700 to 900 nm, so relatively little light energy is absorbed when these wavelengths are introduced to tissue. However, two chromophores, oxy-Hb and deoxy-Hb, strongly absorb light within the "optical window" from 700 to 900 nm. The relative concentration of these two chromophores in the brain's blood supply are linked to neural activity, and therefore can be utilized to serve as biologically relevant markers with which to monitor neural activity and detect deception.

A continuous wave (CW) fNIR spectroscopic system is utilized to detect deception. It is to be understood, however, that other types of fNIR spectroscopic systems are applicable, such as a frequency domain (FD) system and a time resolved (TR) system, for example. In a CW fNIR spectroscopic system, infrared light is provided at a relatively constant intensity during a measurement period. Reflected energy is detected and the intensity levels of the reflected energy are analyzed. In a FD fNIR spectroscopic system, infrared energy at a specific frequency is provided and the amplitude and phase of the reflected energy are analyzed. In a TR fNIR spectroscopic system, a time limited pulse is provided and the pulse length of the reflected energy is analyzed. Use of a CW fNIR system to detect deception provides the ability to make quantitative measurements of hemodynamic changes during brain activation under ambulant conditions. In an example configuration, multiple source-detector pairs, or optodes, are placed about the head of a subject. In an example embodiment, activity from brain tissue at depths from 1 to 5 centimeters (cm) is measurable.

FIG. 1 is a schematic diagram of an example functional near-infrared sensing device 30 for deception detection. The sensing device 30 comprises at least one source 22 and at least one detector 24. Elements labeled "22" represent light sources. Elements labeled "24" represent light detectors. Each source-detector pair (labeled 1 through 16) is referred to as an "optode." The sensing device 30 can be configured in any appropriate shape and size. In an example configuration, the sensing device 30 is configured as a flexible sensing device that can be positioned on the head of a subject. In an example configuration, the sensing device 30 comprises an array of sources 22 and detectors 24. Each source 22 is configured to provide optical energy at a specific wavelength(s) in the near-infrared range. Each source 22 can comprise a light emitting diode (LED), or the like. In an example embodiment, each source 22 is configured to provide optical energy having a wavelength within the band of 700 to 900 nanometers (nm), inclusive. Each detector 24 is configured to receive optical energy at or near-infrared wavelengths. Each detector 24 can comprise a photodetector, or the like. In an example embodiment, each detector 24 is configured to receive optical energy having a wavelength within the band of 700 to 900 nm, inclusive. The configuration of sensing device 30 depicted in FIG. 1 comprises four sources 22 and ten detectors 24. The configuration of the four sources 22 and ten detectors 24, as depicted in FIG. 1, forms sixteen optical nodes (optodes) 20, which are labeled 1 through 16, respectively. It is emphasized, that the configuration of sources, detectors, and optodes, as depicted in FIG. 1 is exemplary. Any appropriate configured can be utilized, such as utilizing more or less detectors per optode, more or less sources per optode, and/or utilizing more or less optodes per sensing device, for example.

FNIR technology employs specified wavelengths in the optical window that easily pass through most tissue, but reflect back from oxy- and deoxy-Hb. Because photons scatter in a relatively predictable pattern, they can be measured using the sensing device 30 with photodetectors 24 on the surface of the skin. The relative levels of absorption and backscatter from oxy and deoxy-Hb provide information about neural activity in the cortex. In an example embodiment, the depth of imagery is equal to approximately half the distance between source 22 and photodetector 24. In this embodiment, because light attenuation increases exponentially with increasing depth of penetration, the maximal depth for imagery for cognitive, emotional, or motivational activity is about 2-3 cm, which allows imagery of much of the cortical surface. Typically, the sensing device 30 will comprise at least one source 22, which irradiates the tissue, and at least one photodetector 24 that receives light after it has interacted with the tissue. Together these are used to create the optodes 20. Several types of brain function can be assessed using fNIR, including motor and visual activation, auditory stimulation and the performance of various cognitive, emotional, and/or motivational tasks.

Figure 2:
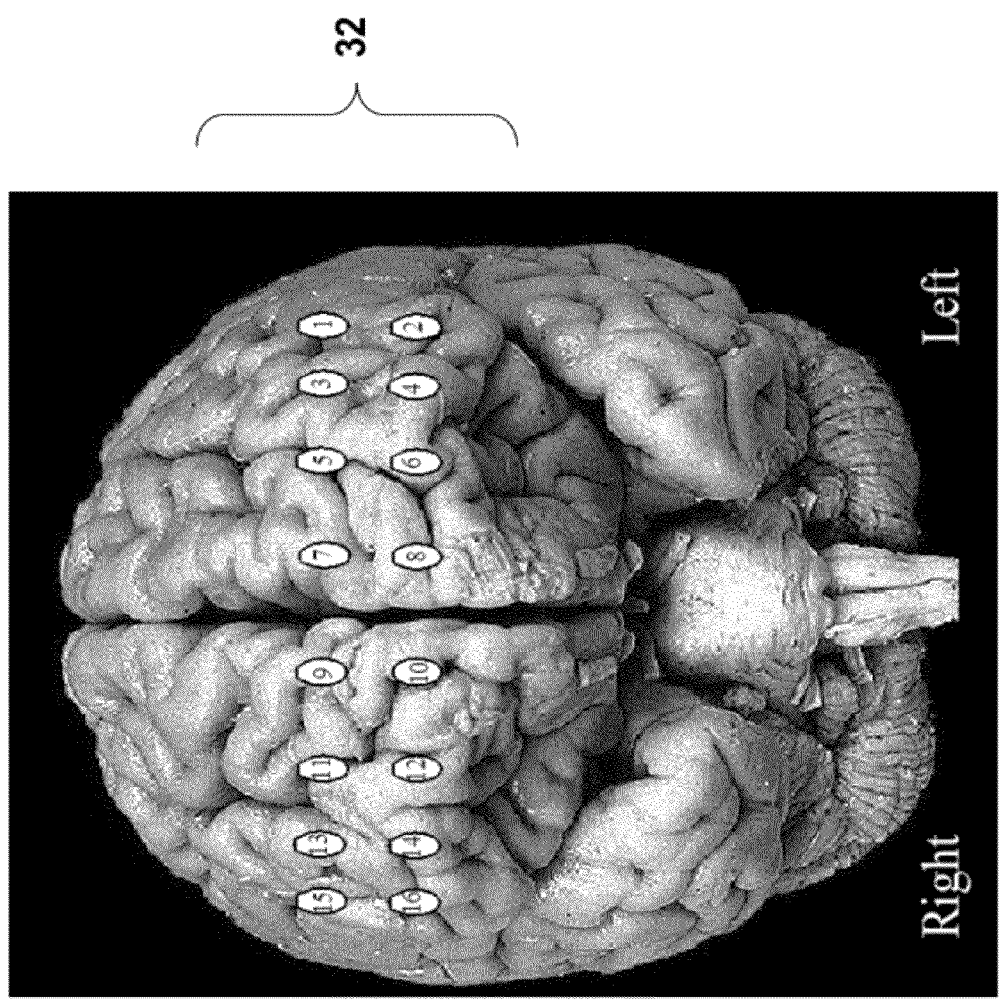
FIG. 2 depicts example locations of a brain proximate to which optodes 20 of the functional near-infrared sensor device 30 are positioned to detect deception.

FIG. 2 depicts example locations of a brain proximate to which optodes 20 of the functional near-infrared sensor device 30 are positioned to detect deception. The sensing device 30 is positioned around the head approximately area 32, and optodes 1 through 16 are aligned with respective areas of the cortex labeled in FIG. 2 as 1 through 16. When appropriate questioning technique is utilized, and appropriate signal processing is applied to the neural measures, activity in specific areas of the brain is indicative of deliberate deception. In an example embodiment, activity in the inferior and/or middle prefrontal cortical areas of the brain, such as the bilateral dorsolateral prefrontal and/or inferior frontal cortex, is measured for an indication of deliberate deception. In a more specific example embodiment, activity in the bilateral inferior frontal gyri (the convolutions on the surfaces of the cerebral hemispheres) and the middle frontal gyri, is measured for an indication of deliberate deception. These cortical areas are active during response inhibition and changes in response strategies, in both working and episodic memory. Additional areas of activation include superior frontal gyri. Thus, the sensing device 30 can be utilized to target responses from these areas to detect deception. The alignment/positioning of the optodes 20 can be accomplished in any appropriate manner. Also, optodes can be realigned. For example, data received from the optodes 20 can be utilized to determine which areas of the brain are providing relevant responses with respect to deception indication and the optodes 20 can be realigned accordingly.

Figure 3:
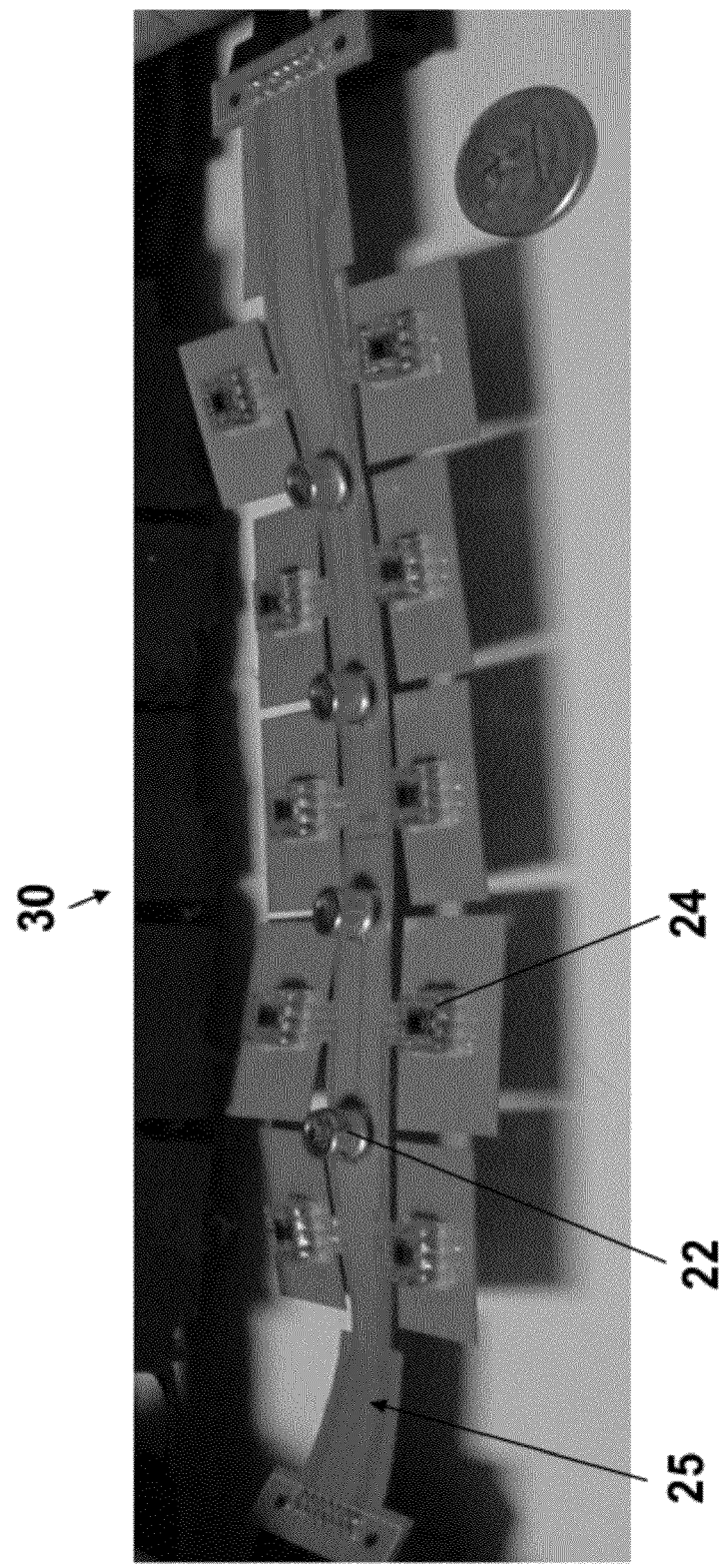
FIG. 3 shows a specific implementation of an example sensing device 30 in the form of a flexible belt-like apparatus.

FIG. 3 shows a specific implementation of an example sensing device 30 in the form of a flexible belt-like apparatus. The sensing device 30 can be held together by an appropriate means such as a reusable, flexible belt 25 to which the sources 22 and detectors 24 are attached. Only one source 22 and detector 24 are labeled as such in FIG. 3 for the sake of simplicity. Detectors 24 can comprise circuitry, such as circuit boards or the like, as shown in FIG. 3. In example configuration, the detectors 24 are attached to the flexible belt 25, as shown in FIG. 3, forming gaps between each detector 24 to permit deformation of the sensing device 30 to conform to the head of a subject. The flexible belt 25 permits sensor 30 to be placed around a subject's head for taking measurements of cortical responses.

Figure 4:
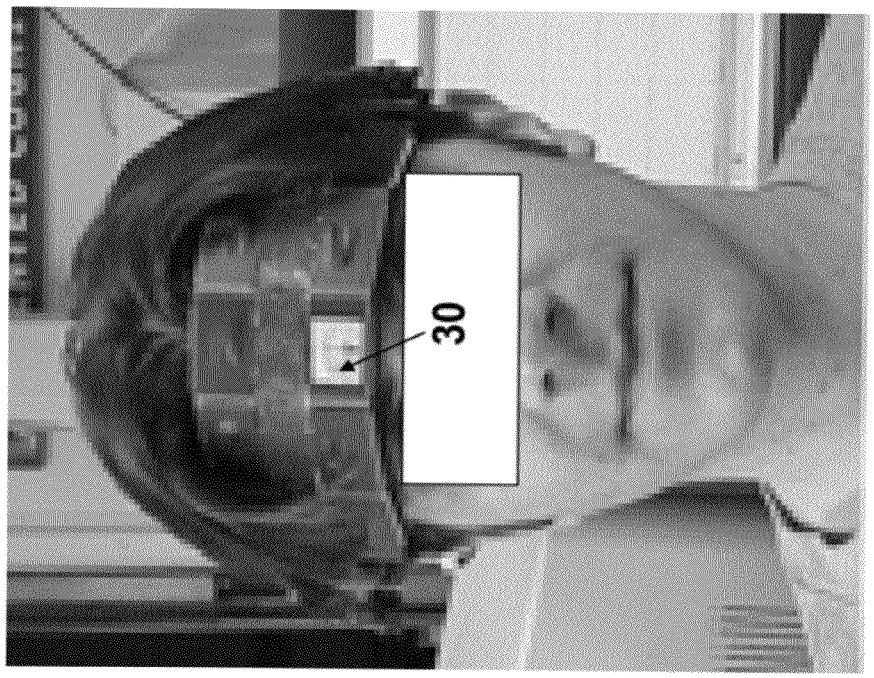
FIG. 4 shows the specific implementation of the sensing device 30, including the flexible belt 25, positioned about the head of a subject.

FIG. 4 shows the specific implementation of the sensing device 30, including the flexible belt 25, positioned about the head of a subject. The flexible belt 25 can include suitable circuitry, not shown in FIG. 3, for providing power to sources 22 and detectors 24. The flexible belt 25 can also include suitable circuitry for routing response information from the detectors 24 to a suitable processor or the like for analyzing data received by the detectors 24. The detectors 24 can provide signals wireless and/or via wired connections.

In an example embodiment, cushioning material or the like can be positioned around the sources 22 and the detectors 24 to provide cushioning between the subject's head and the sensing device 30. The cushioning material can be relatively inexpensive and disposable, thus providing a hygienic, comfortable, inexpensive reusable apparatus for data collection.

Figure 5:
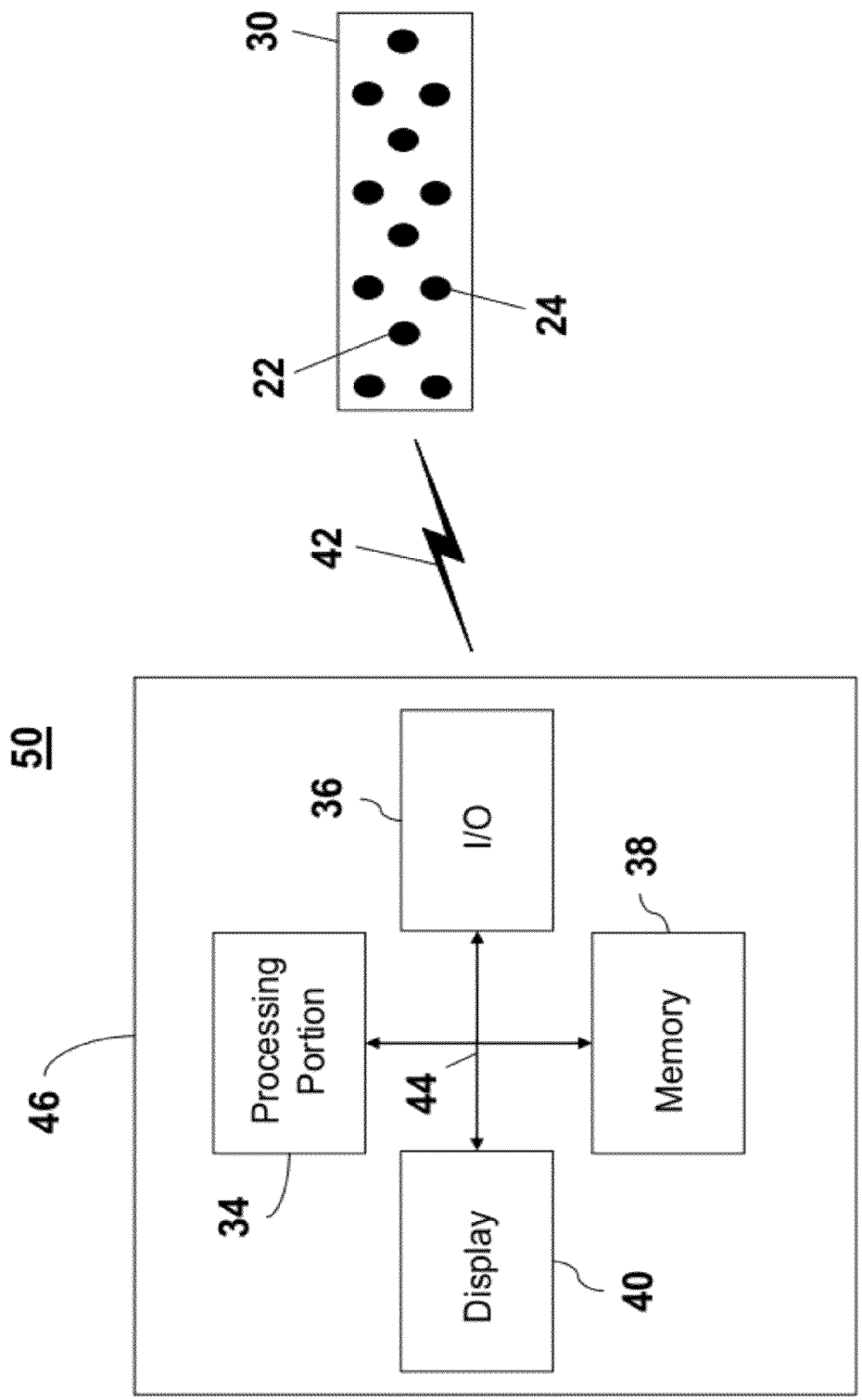
FIG. 5 is a block diagram of an example system 50 for detecting deception via functional near-infrared spectroscopy.

FIG. 5 is a block diagram of an example system 50 for detecting deception via functional near-infrared spectroscopy. The system 50 comprises a processor 46 and the sensing device 30. The processor 46 comprises a processing portion 34, a memory portion 38, an input/output portion 36, and optionally, a display portion 40. The processing portion 34, the memory portion 38, the input/output portion 36, and the display portion 40 are in communication via interface 44. The interface 44 can be a wired interface, a wireless interface, or a combination thereof. It is emphasized that the block diagram depicted in FIG. 5 is exemplary and not intended to imply a specific implementation. Thus, the system 50 can be implemented in a single processor or multiple processors. Multiple processors can be distributed or centrally located.

Multiple processors can communicate wirelessly, via hard wire, or a combination thereof.

The processor 46 can comprise any appropriate device for receiving information from the sensing device 30 and for analyzing the received information. Examples of appropriate devices include computers, mainframes, personal computers ("PCs"), server computers, gaming platforms, mobile communications devices, mobile telephones, lap top computers, handheld processors, portable media players, portable computing devices, such as laptops, personal digital assistants ("PDAs"), cell phones, portable email devices, thin clients, portable gaming devices, consumer electronic devices, such as TVs, DVD players, set top boxes, monitors, displays, public computing devices, such as kiosks, or a combination thereof. The processor 46 is coupled to the sensing device 30 via interface 42. The interface 42 can comprise any appropriate interface, such as a wireless interface and/or a wired interface.

Wireless transfer between the processor 46 and the sensing device 30 is advantageous in indoor scenarios such as criminal interrogations for courts, forensic applications, as well as field deployment scenarios such as credibility assessment of informants or criminal checks at border crossings, ports or schools, and airport security, for example. A wireless design also provides an environment wherein relevant information can be accessed by several people in real time.

The processor 46 is capable of performing the operations associated with detecting deception via fNIR spectroscopy. For example, the processing portion 34 is capable of receiving data, via the input/output portion 36, from the sensing device 30, and determining if deception has occurred. The memory portion 38 is capable of storing all parameters associated with detecting deception via fNIR spectroscopy. The input/output portion 46 is capable of providing and/or receiving data associated with detecting deception via fNIR spectroscopy. The display portion 40 is configured to render the information indicative of the occurrence, or lack thereof, of deception.

Depending upon the exact configuration and type of processor, the memory portion 38 can be volatile (such as RAM and/or cache), non-volatile (such as ROM, flash memory, etc.), or a combination thereof. The computing device 46 can have additional features/functionality. For example, the computing device 46 can include additional storage (e.g., removable storage and/or non-removable storage) including, but not limited to, magnetic or optical disks, tape, flash, smart cards or a combination thereof. Computer storage media include volatile and nonvolatile, removable and non-removable media implemented in any method or technology for storage of information such as computer-readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, universal serial bus (USB) compatible memory, smart cards, or any other medium which can be used to store the desired information and which can be accessed by the computing device 36. Any such computer storage media can be part of the computing device 46.

The computing device 46 also can contain communications connection(s) that allows the computing device 46 to communicate with another computing device (e.g., the fNIR sensing device 30). A communications connection(s) is an example of communication media. Communication media typically embody computer readable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared and other wireless media. The term computer readable media as used herein includes both storage media and communication media. The computing device 46 also can have input devices such as keyboard, mouse, pen, voice input device, touch input device, etc. Output devices such as a display, speakers, printer, etc. also can be included.

Figure 6:
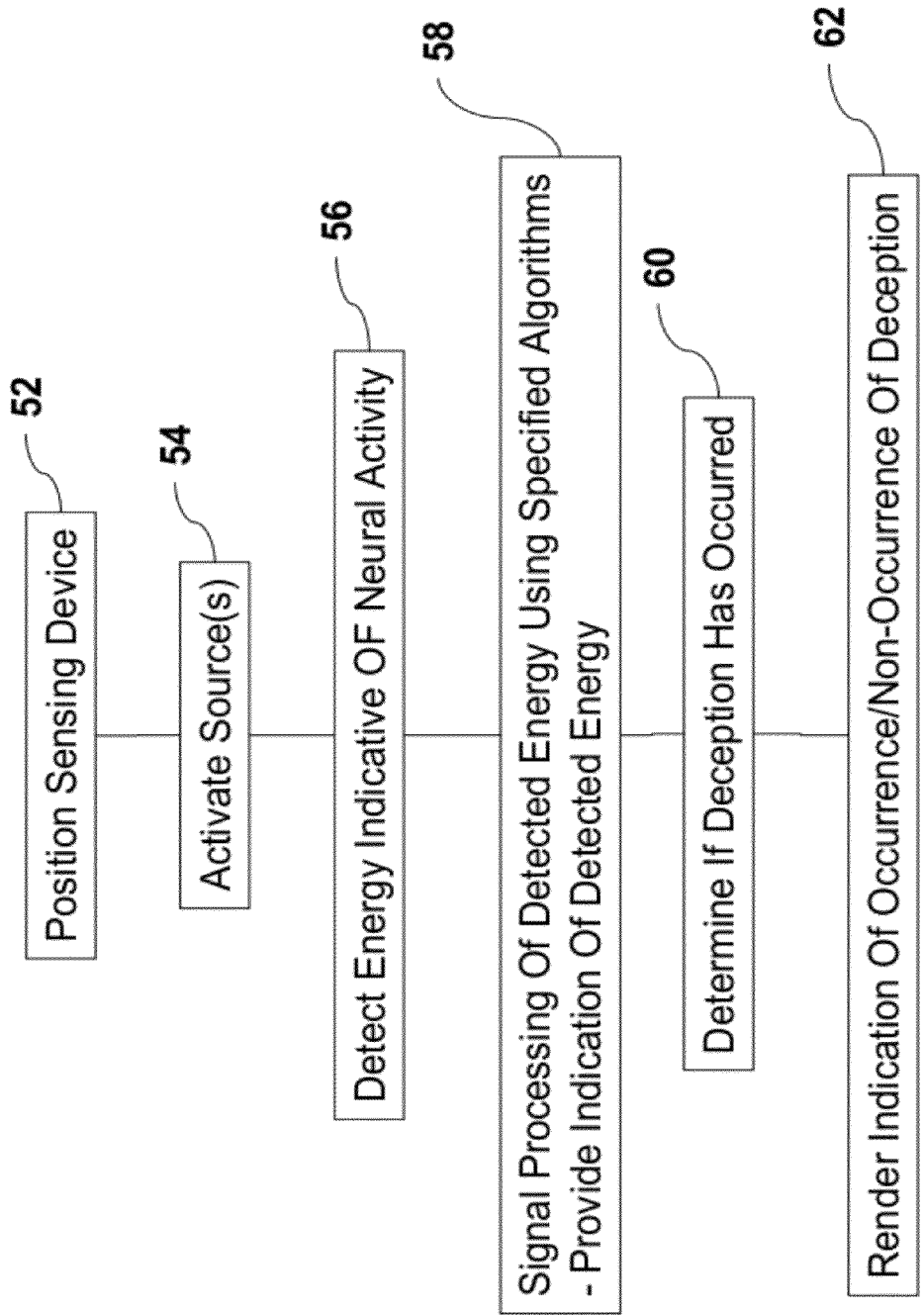
FIG. 6 is a flow diagram of an example process for detecting deception via functional near-infrared spectroscopy.

FIG. 6 is a flow diagram of an example process for detecting deception via functional near-infrared spectroscopy. The sensing device, such as the sensing device 30 for example, is position on the subject at step 52. The sensing device can be positioned at any appropriate location and orientation. In an example embodiment, the sensing device is positioned on the head, or scalp, of the subject and the optodes of the sensing device are aligned proximate to areas of the cortex to detect neural activity associated with the occurrence of deception. In another embodiment the sensing device can be positioned in proximity to the head or scalp, functioning as a remote sensing device. These areas can include, for example, inferior prefrontal cortical areas of the brain, middle prefrontal cortical areas of the brain, the bilateral dorsolateral prefrontal cortex, bilateral inferior frontal gyri, middle frontal gyri, and/or superior frontal gyri.

At least one source, such as source 22 for example, of the sensing device is activated at step 54. In an example embodiment, activation of a source comprises providing optical energy, such as near-infrared energy. In one example embodiment, optical energy having a wavelength in the range of 700 to 900 nm, inclusive, is provided. At step 56, reflected near-infrared radiation is received by the sensing device, by detectors 24 for example. The reflected energy is indicative of neural activity associated with deception. More specifically, the reflected optical energy is indicative of changes in the concentration of deoxygenated hemoglobin and oxygenated hemoglobin. In an example embodiment, detected reflected energy comprises optical energy, such as near-infrared energy, having a wavelength in the range of 700 to 900 nm, inclusive. An indication of the detected energy is provided to a processor, such as the processor 46 for example, at step 58. In an example embodiment, the detected optical energy is converted, or transduced, to electrical energy, and the electrical energy is provided to the processor.

At step 60, the occurrence, or non-occurrence, of deception is determined. Data, indicative of the provided electrical energy is analyzed to determine the level of activity in key areas of the brain and correlated to specific instances in which deception may be taking place. In an example embodiment, the data is low-pass filtered to remove noise. Noise can be due to variety of causes, such as respiration and/or cardiac variation of the subject, or subject movement, for example. The low-pass filter can be implemented with any appropriate cut-off frequency, such as 0.4 Hertz (Hz) for example. Data is collected from each optode for a period of time (referred to as an epoch) during which an event occurs. The term "event" refers to the occurrence of a subject's statement that is being evaluated. In an example embodiment, data is collected from each optode for a period of 18 seconds, representing a 6 second time period prior to an event (pre-stimulus time segment) and a 12 second time period subsequent the event (post-stimulus segment). It is emphasized that these time segment lengths are examples. For each optode, the epochs collected during multiple events are averaged. Each average epoch is baseline corrected by subtracting the mean value of the average epoch from the average epoch. Outliers beyond the limit of typical physiological reactivity may be removed. Statistical analyses are performed on the epochs to determine if deception, or the lack thereof, has occurred. Further, because the subject has the ability to provide known, truthful responses, as well as directed lies, such responses can be used as a baseline for a particular subject in order to more clearly identify deception by comparison of data obtained for truthful responses to data obtained for other responses. Because there are individual differences in the magnitude of neural responses, as well as the precise localization of the response, this technique allows the examiner to adjust both the localization and the magnitude of neural responses to questions with unknown lie/truth status by using the localization and the magnitude of responses to questions with known lie/truth status.

Figure 7:
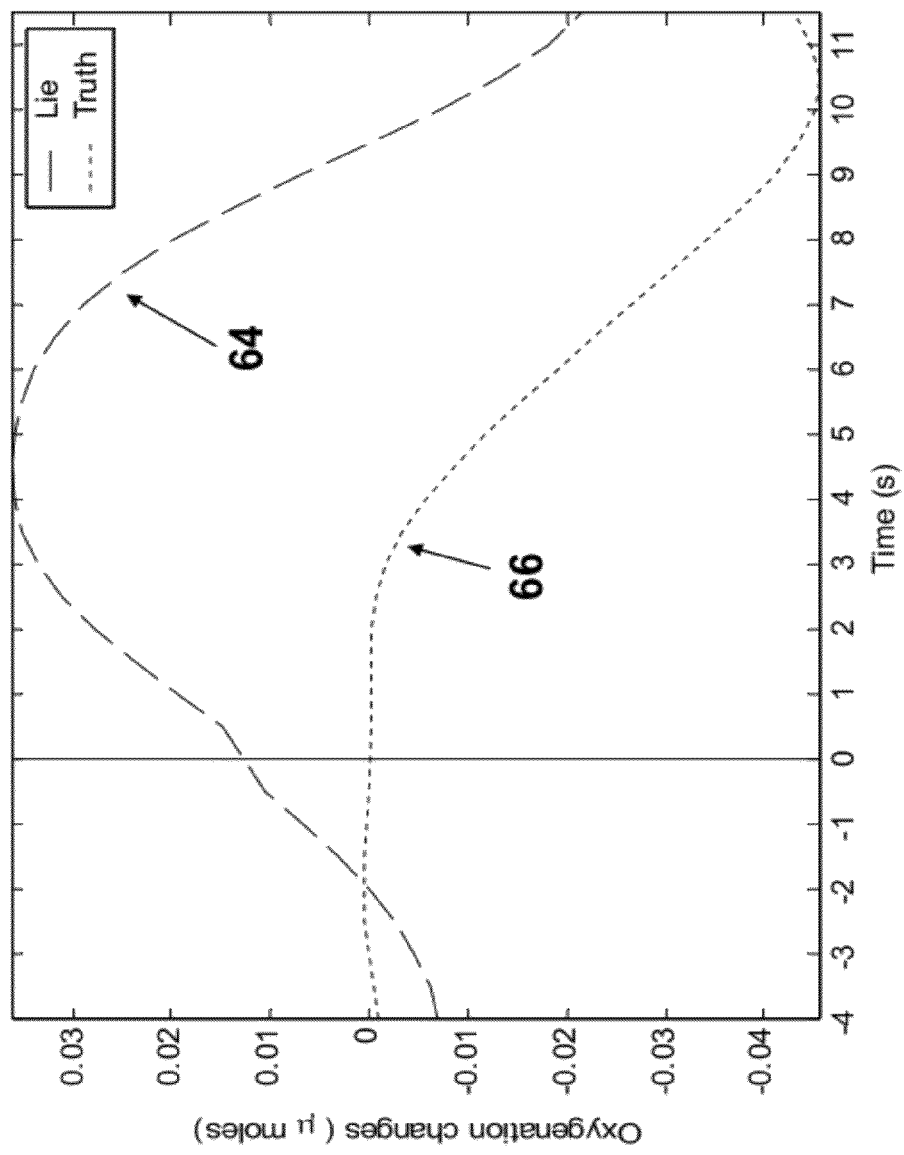
FIG. 7 is an example graph depicting oxygenation levels at the left frontal gyri.

In an example embodiment, the occurrence, or non-occurrence, of deception (a lie, malingering, etc.) is determined by comparing oxygenation levels associated with an event with oxygenation levels associated with a known truth. In an example embodiment, if the oxygenation level associated with an event differs from the oxygenation level associated with a known truth, it is determined that deception has occurred. Oxygenation levels associated with a lie can be greater than or less than oxygenation levels associated with a truth. In an example embodiment, if the oxygenation level associated with an event is greater than the oxygenation level associated with a known truth, it is determined that deception has occurred. For example, FIG. 7 is an example graph depicting oxygenation levels at the left frontal gyri. The graph in FIG. 7 depicts oxygenation levels in moles versus time in seconds. The time labeled zero represents the occurrence of the event. The dashed line 64 represents levels associated with the subject telling a lie and the dotted line 66 represents oxygenation levels associated with the subject telling the truth. Thus, it can be determined that deception has occurred because the levels of line 64 are greater than the levels of line 66 after the occurrence of the event (time 0). Also, an appropriate threshold value of oxygenation level separating a lie (line 64) from a truth (line 66) can be utilized to determine if deception has occurred.

Figure 8:
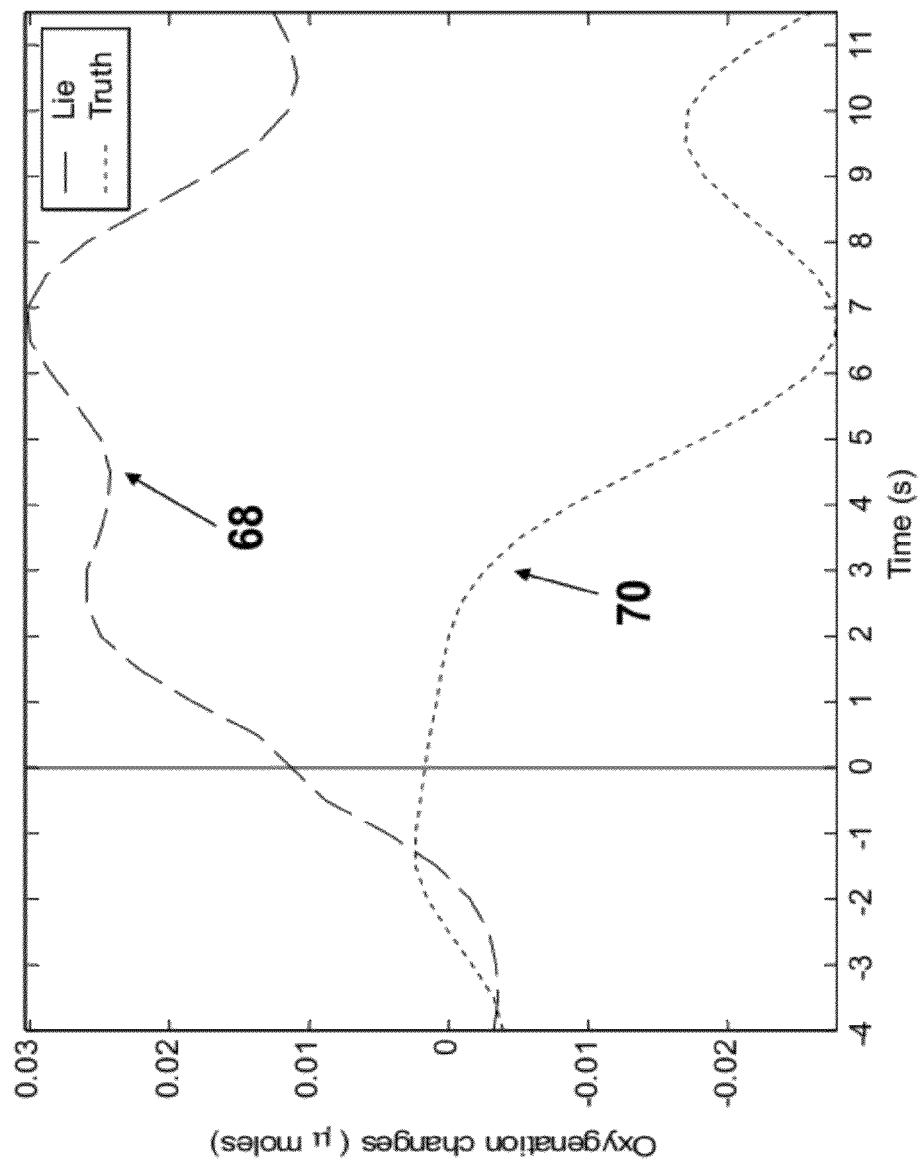
FIG. 8 is an example graph depicting oxygenation levels at the right frontal gyri.

The determination as to whether an event represents deception (a lie, malingering, etc.) or the truth can be dependent upon the area of the brain being measured. FIG. 8 is an example graph depicting oxygenation levels at the right frontal gyri. The graph in FIG. 8 depicts oxygenation levels in moles versus time in seconds. The time labeled zero represents the occurrence of the event. The dashed line 68 represents levels associated with the subject telling a lie and the dotted line 70 represents oxygenation levels associated with the subject telling the truth. Thus, it can be determined that deception has occurred because the levels of line 68 are greater than the levels of line 70 after the occurrence of the event (time 0). Also, an appropriate threshold value of oxygenation level separating a lie (line 68) from a truth (line 70) can be utilized to determine if deception has occurred.

At step 62, instances of probable deception and/or lack thereof, are recorded, rendered (on the display portion 40 for example) and/or conveyed to the person administering the test or, alternatively, to an interested third party.

Accordingly, fNIR imaging is utilized to reliably discriminate when individuals are lying from when they are telling the truth. Lying is associated with increased oxygenation relative to telling the truth in the inferior and/or middle prefrontal cortical areas of the brain. In an example embodiment, the cortex is imaged with fNIR, and imaging of other areas of the brain is used in conjunction therewith to determine the occurrence of deception. For example function magnetic resonance imaging (fMRI) can be utilized to measure the anterior cingulate cortex and/or the limbic areas, along with fNIR measurements of the inferior and/or middle prefrontal cortical areas of the brain, to determine if deliberate deception has occurred.

Because the very experience of being questioned is likely to evoke an emotional response, and specific questions about certain activities are likely to evoke strong emotions, the type of questions that are asked and the method of question comparison that are employed are determinative to the reliability of the inferential process. Also determinative of the reliability of the inferential process are the length of the question being asked and the time period after the event (question) that is analyzed. For example, questions presented aurally are extended in time, and the capacity to average is dependent on a consistent time-lock. Different length questions result in different brain processing patterns with respect to the planned response. As such, averaging produces "jitter" or "noise" in the peak of the brain response, lowering the ability to distinguish deception from truth. Utilization of the attestation affirmation question minimizes or eliminates this variance in brain responses that might be due to the length or form of critical questions, or the differences in form between a critical question and a control question. The attestation affirmation allows the direct comparison of brain responses to identical questions with a YES or NO answer format. The distinction between a truthful response and a false response then is a result of with the examinee's knowledge about how she or he answered the former question. In addition, the use of the visual presentation of any question with which the examinee has been well familiarized, thereby allowing relatively instantaneous recognition of the question, allows precise time-locks for averaging the brain response across multiple questions.

Figure 9:
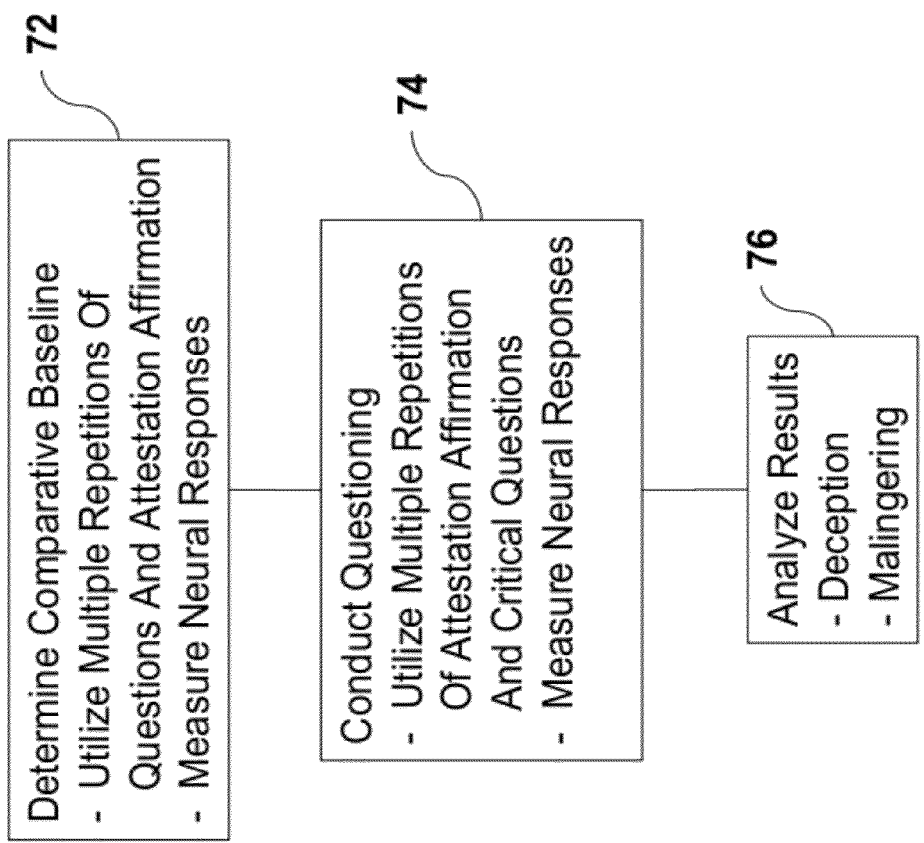
FIG. 9 is a flow diagram of an example process for assessing credibility, detecting deception, and implementing a query methodology via neuroimaging detection deception and/or malingering utilizing an attestation affirmation.

FIG. 9 is a flow diagram of an example process for assessing credibility, detecting deception, and implementing a query methodology via neuroimaging detection deception and/or malingering utilizing an attestation affirmation. The process depicted in FIG. 9, provides a method of questioning and measurement that allows sufficiently accurate determinations to be made when using fNIR spectroscopy, or other brain imaging technologies, to assess credibility, to infer deception, or to infer malingering (faking a symptom). The questioning and measurement process comprises determining a comparative baseline at step 72. The baseline establishes neural responses for known truthful responses and/or and neural responses for known false responses. The baseline is utilized for comparison with responses obtained during questioning. In an example embodiment, during establishment of the baseline, as explained in more detail below, multiple repetitions of attestation affirmation type cues are utilized. The utilization of a comparative baseline refers to a method whereby an individualized level of neurophysiological response is established by asking the examinee to lie to questions with known answers during a preliminary test period, prior to asking the examinee critical questions with unknown answers during the formal questioning period. The differential neurophysiological response when falsely answering questions with known answers is then used as a comparison for critical questions with unknown answers.

The questioning phase, at step 74, comprises asking multiple critical questions and affirmation attestations and measuring the associated neural responses. Because neuroimaging is being utilized, no limit is placed on the number of critical questions, attestation affirmation cues, or questions in general, that can be asked. At step 76, the results obtained during the questioning phase at step 74 are compared with the baseline obtained at step 72 to determine if deception has occurred and/or if malingering has occurred. That is, the differential neurophysiological response when falsely answering questions with known answers is used as a comparison for critical questions with unknown answers. It is to be understood that the process depicted in FIG. 9 is applicable to various types of brain imaging technologies and psychophysiological measures, such as functional near-infrared tomography, functional magnetic resonance imaging (fMRI), positron emission tomography (PET), single positron emission computed tomography (SPECT), event-related brain potentials (ERPs), event-related synchronization or desynchronization of bandwidths within the electroencephalogram (EEG, ERS or ERD), magnetoencephalography (MEG), as well as other forms of brain imaging techniques or their variations, for example.

fNIR based polygraphy provides the ability to measure central nervous system correlates of deceptive processes. The use of fNIR allows an examiner to repeatedly ask the same question without habituation and loss of the neurophysiological response required to distinguish between truthful and deceptive answers. For example, a question can be repeated 10 to 15 times when using fNIR. Question repetition improves the ability to distinguish between signals associated with truthful and deceptive responses as compared to asking a question a single time. This is due, in part, to the ability to average out the noise or background brain activations that are not related to the question of concern, and/or anomalies in the signals. Repeating identical questions minimizes variance in the brain response due to the processing of different linguistic features that is necessary if a variety of distinct questions must be asked.

Further, the capacity to repeat questions allows the utilization of repeated comparative attestation affirmations. This process depicted in FIG. 9 utilizes attestation affirmations multiple times during both the baseline period (step 72) and the formal questioning period (step 74).

Figure 10:
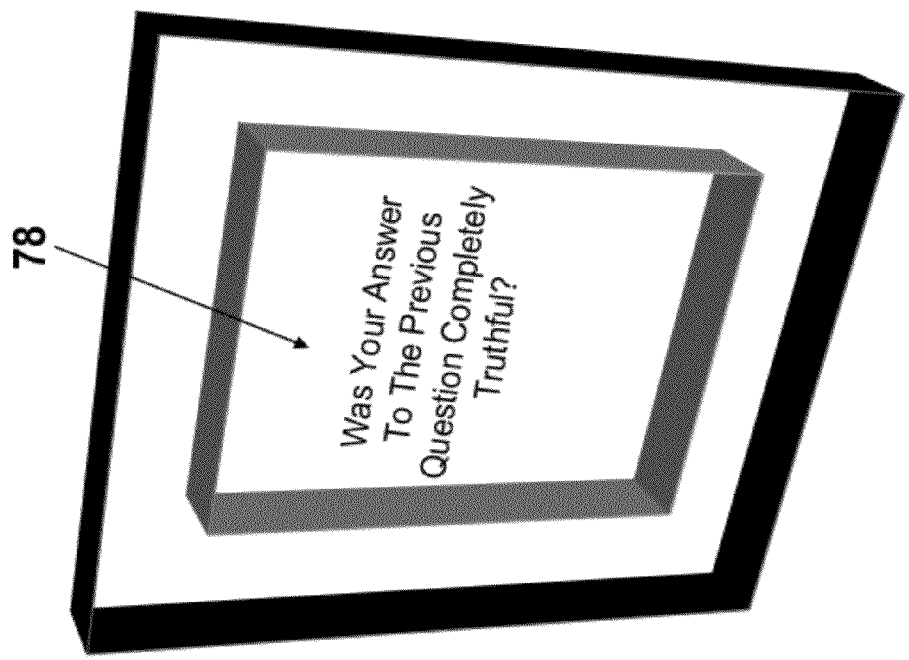
FIG. 10 is a depiction of an example attestation affirmation in the form of a visual cue comprising text.
Figure 10:

As previously described, an attestation affirmation can be in the form of an audio or visual cue. FIG. 10 is a depiction of an example attestation affirmation 78 in the form of a visual cue comprising text. The text can comprise any appropriate text that queries the examinee as to the truthfulness of the previous response. As shown in FIG. 10, the attestation affirmation comprises a visual representation of the text "Was Your Answer To The Previous Questions Completely Truthful?". Utilization of an attestation affirmation minimizes or eliminates variance in brain responses that might be due to the length or form of a question, or the specific affective response to any given question. The attestation affirmation allows the direct comparison of brain responses to identical questions with a YES-NO answer format, with the distinction between a truthful response and a false response being the examinee's knowledge about how they answered the former question. When the examinee sees the visual indication of the attestation affirmation, the examinees neurological response is relatively immediate. The neurological response is not delayed because the examinee must listen to an audio indication of the attestation affirmation. Also, the neurological response is not drawn out or distorted because of the time needed to provide an audio indication of the attestation affirmation.

Figure 11:
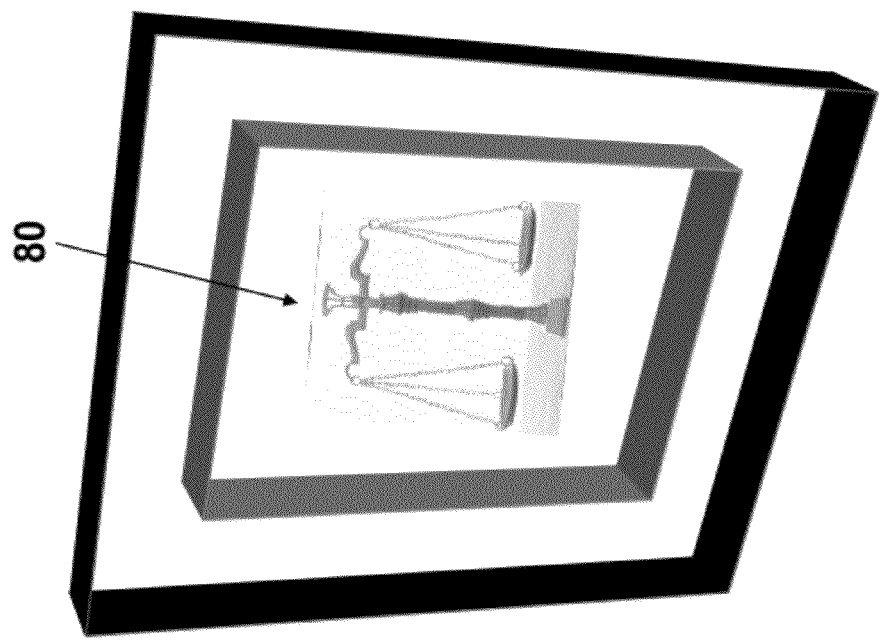
FIG. 11 is a depiction of an example attestation affirmation in the form of a visual cue comprising an icon.
Figure 11:
Figure 12:
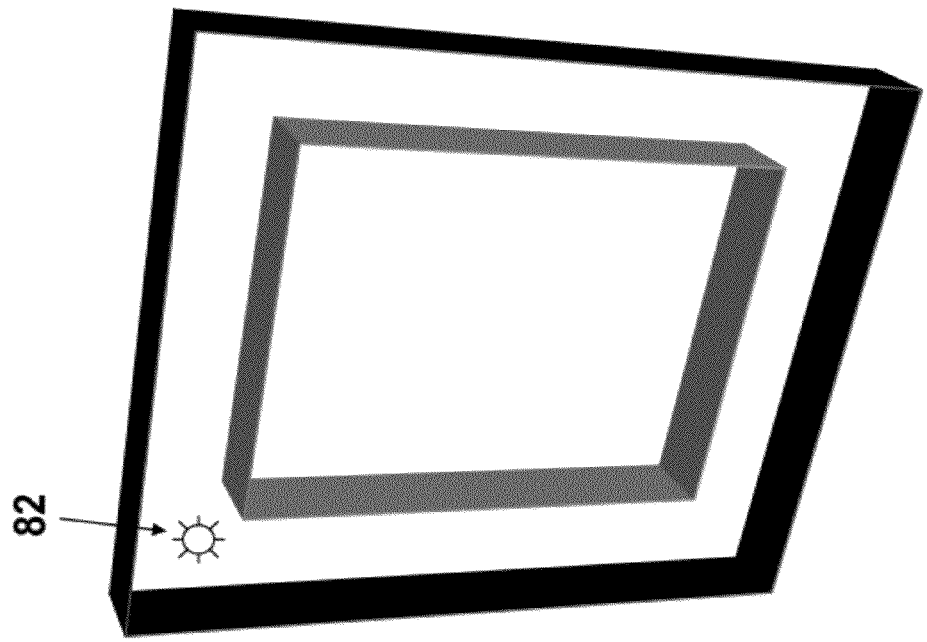
FIG. 12 is a depiction of an example attestation affirmation in the form of a visual cue comprising a light.
Figure 12:

The examinee can be trained to recognize any appropriate visual cue indicating an attestation affirmation. For example, the visual cue indicating an attestation affirmation can comprise an icon or the like 80, as depicted in FIG. 11. As another example, the visual cue indicating an attestation affirmation can comprise a light (or blinking light) 82, as depicted in FIG. 12. Providing a visual cue that is more quickly recognized by the examinee can provide more consistent results.

The attestation affirmation can be in the form of an audio cue. For example, the examiner can ask the examinee "Was your answer to the previous question completely truthful?" Also, in an attempt to achieve more immediate and less variant neurological results, the audio cue of the attestation affirmation can be in the form of any sound such as a tone, a beep, or the like). Thus, once trained, the examinee would immediately recognize the audio cue as an indication of an attestation affirmation.

While example embodiments of credibility assessment, deception detection, and a query methodology for determining deception via neuroimaging have been described in connection with various computing devices/processor, the underlying concepts can be applied to any computing device, processor, or system capable of credibility assessment, deception detection, and a query methodology for determining deception via neuroimaging. The various techniques described herein can be implemented in connection with hardware or software or, where appropriate, with a combination of both. Thus, the methods and apparatuses for credibility assessment, deception detection, and a query methodology for determining deception via neuroimaging, or certain aspects or portions thereof, can take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for credibility assessment, deception detection, and a query methodology for determining deception via neuroimaging. In the case of program code execution on programmable computers, the computing device will generally include a processor, a storage medium readable by the processor (including volatile and non-volatile memory and/or storage elements), at least one input device, and at least one output device. The program(s) can be implemented in assembly or machine language, if desired. The language can be a compiled or interpreted language, and combined with hardware implementations.

The methods and apparatuses for credibility assessment, deception detection, and a query methodology for determining deception via neuroimaging also can be practiced via communications embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, or the like, the machine becomes an apparatus for credibility assessment, deception detection, and a query methodology for determining deception via neuroimaging. When implemented on a general-purpose processor, the program code combines with the processor to provide a unique apparatus that operates to invoke the functionality of credibility assessment, deception detection, and a query methodology for determining deception via neuroimaging. Additionally, any storage techniques used in connection with credibility assessment, deception detection, and a query methodology for determining deception via neuroimaging can invariably be a combination of hardware and software.

While credibility assessment, deception detection, and a query methodology for determining deception via neuroimaging has been described in connection with the various embodiments of the various figures, it is to be understood that other similar embodiments can be used or modifications and additions can be made to the described embodiment for performing the same function of credibility assessment, deception detection, and a query methodology for determining deception via neuroimaging without deviating therefrom. Therefore, credibility assessment, deception detection, and a query methodology for determining deception via neuroimaging should not be limited to any single embodiment, but rather should be construed in breadth and scope in accordance with the appended claims.

What is claimed:

1. A method comprising:
   measuring near-infrared optical energy indicative of oxygenation levels in a blood supply of a cortex of a brain of a subject to obtain a plurality of neural responses of the subject each time the subject answers a question of a respective plurality of questions, wherein at least one of the plurality of questions is repeated a plurality of times;
   measuring near-infrared optical energy indicative of oxygenation levels in the blood supply of the cortex of the brain of the subject to obtain a neural response of the subject associated with the subject's response to a visual cue of an affirmation attestation, wherein the affirmation attestation is indicative of a query as to the truthfulness of a response to a previous one of the plurality of questions;
   comparing the oxygenation levels indicated by the measured near-infrared optical energy with a baseline oxygenation level, wherein the baseline oxygenation level is indicative of one of a known truthful response or a known false response; and
   if the oxygenation levels indicated by the measured near-infrared optical energy differs from the baseline oxygenation level, determining that the subject conducted at least one of deception in response to a question or malingered in response to a question.

2. The method of claim 1, further comprising:
   positioning a sensing device proximate to a scalp of the subject;
   providing near-infrared optical energy directed toward the scalp; and
   in response to providing near-infrared optical energy, receiving reflected near-infrared optical energy indicative of the oxygenation level in the blood supply of the cortex of the brain of the subject.

3. The method of claim 2, wherein the near-infrared optical energy is provided at a relatively constant intensity.

4. The method of claim 1, further comprising:
   converting the received near-infrared optical energy to electrical energy; and
   providing a signal indicative of the electrical energy for determining if the subject conducted deception.

5. The method of claim 1, wherein the baseline oxygenation level is an oxygenation level associated with the subject telling a truth.

6. The method of claim 1, further comprising determining the subject conducted deception if the oxygenation level indicated by the received near-infrared optical energy is greater than the baseline oxygenation level.

7. The method of claim 1, wherein the near-infrared optical energy comprises a wavelength in the range of 700 to 900 nanometers, inclusive.

8. The method of claim 1, wherein the cortex of the brain comprises at least one of a dorsolateral prefrontal cortex and an inferior frontal cortex.

9. The method of claim 1, wherein the oxygenation level in the blood supply of the cortex is indicative of at least one of deoxygenated hemoglobin and oxygenated hemoglobin.

10. A system comprising:
    a sensing device configured to:
      sense near-infrared optical energy indicative of oxygenation levels in a blood supply of a cortex of a brain of a subject;
    a processor; and
    a memory coupled to the processor, the memory having stored thereon executable instructions that when executed by the processor cause the processor to perform operations comprising:
      measuring the near-infrared optical energy indicative of oxygenation levels in the blood supply of the cortex of a brain of the subject to obtain a neural response of the subject each time the subject answers a question of a respective plurality of questions, wherein at least one of the plurality of questions is repeated a plurality of times;
      measuring near-infrared optical energy indicative of oxygenation levels in the blood supply of the cortex of the brain of the subject to obtain a neural response of the subject associated with the subject's response to a visual cue of an affirmation attestation, wherein the affirmation attestation is indicative of a query as to the truthfulness of a response to a previous one of the plurality of questions;
      comparing the oxygenation levels indicated by the measured near-infrared optical energy with a baseline oxygenation level, wherein the baseline oxygenation level is indicative of one of a known truthful response or a known false response; and
      if the oxygenation levels indicated by the measured near-infrared optical energy differs from the baseline oxygenation level, determining that the subject conducted at least one of deception in response to a question or malingered in response to a question.

11. The system of claim 10, wherein:
    the sensing device further comprises:
      a flexible portion configured to be positioned proximate to a scalp of the subject;
      at least one source configured to provide near-infrared optical energy directed toward the scalp of the subject; and
      at least one detector configured to receive reflected near-infrared optical energy in response to the provided near-infrared optical energy.

12. The system of claim 10, wherein the sensing device is configured to provide near-infrared optical energy at a relatively constant intensity.

13. The system of claim 10, wherein the sensing device is further configured to:
    convert the received near-infrared optical energy to electrical energy; and
    provide a signal indicative of the electrical energy to the processor.

14. The system of claim 10, wherein the baseline oxygenation level is an oxygenation level associated with the subject telling a truth.

15. The system of claim 10, wherein determining that the subject conducted deception comprises determining if the oxygenation level indicated by the received near-infrared optical energy is greater than the baseline oxygenation level.

16. The system of claim 10, wherein the near-infrared optical energy comprises a wavelength in the range of 700 to 900 nanometers, inclusive.

17. The system of claim 10, wherein the cortex of the brain comprises at least one of a dorsolateral prefrontal cortex and an inferior frontal cortex.

18. The system of claim 10, wherein the oxygenation level in the blood supply of the cortex is indicative of at least one of deoxygenated hemoglobin and oxygenated hemoglobin.

19. A computer-readable storage medium, which is not transient signal per se, having stored thereon executable instructions that when executed by a processor perform operations comprising:
- measuring near-infrared optical energy indicative of an oxygenation levels in a blood supply of a cortex of a brain of a subject to obtain a plurality of neural responses of the subject each time the subject answers a question of a respective plurality of questions, wherein at least one of the plurality of questions is repeated a plurality of times;
- measuring near-infrared optical energy indicative of oxygenation levels in the blood supply of the cortex of the brain of the subject to obtain a neural response of the subject associated with the subject's response to a visual cue of an affirmation attestation, wherein the affirmation attestation is indicative of a query as to the truthfulness of a response to a previous one of the plurality of questions;
- comparing the oxygenation levels indicated by the measured near-infrared optical energy with a baseline oxygenation level, wherein the baseline oxygenation level is indicative of one of a known truthful response or a known false response; and
- if the oxygenation levels indicated by the measured near-infrared optical energy differs from the baseline oxygenation level, determining that the subject conducted at least one of deception in response to a question or malingered in response to a question.

20. The computer-readable storage medium of claim 19, wherein the near-infrared optical energy comprises a wavelength in the range of 700 to 900 nanometers, inclusive.

21. A method for querying an examinee, the method comprising:
- establishing baseline neural responses for the examinee, the baseline neural responses comprising at least one known truthful response and at least one known false response;
- asking the examinee a plurality of questions, wherein at least one of the plurality questions is repeated a plurality of times;
- measuring a respective neural response of the examinee associated with the examinee's response to each of the plurality of questions;
- directly in response to a previous one of the plurality of questions, providing, to the examinee, a visual cue of an affirmation attestation, wherein the affirmation attestation is indicative of a query as to the truthfulness of the response, provided by the examinee, to the previous question;
- measuring a neural response of the examinee associated with the examinee's response to the cue of the attestation affirmation; and
- comparing neural responses associated with the plurality of questions and the visual cue of the affirmation attestation with the baseline neural responses to determine if the examinee at least one of conducted deception in response to a question or malingered in response to a question.

22. The method in accordance with claim 21, wherein the visual cue of an affirmation attestation comprises displayed text.

23. The method in accordance with claim 21, wherein the visual cue of an affirmation attestation comprises a displayed icon.

24. The method in accordance with claim 21, wherein the visual cue of an affirmation attestation comprises a light.

25. A computer readable storing medium that is not a transient signal per se, the computer readable storage medium having stored thereon executable instructions that when executed by a processor perform operations comprising:
- storing baseline neural responses for the examinee, the baseline neural responses comprising at least one known truthful response and at least one known false response;
- measuring a respective neural response of the examinee associated with the examinee's response to each of a plurality of questions, wherein at least one of the plurality questions is repeated a plurality of times;
- directly in response to a previous one of the plurality of questions, providing, to the examinee, a visual cue of an affirmation attestation, wherein the affirmation attestation is indicative of a query as to the truthfulness of the response, provided by the examinee, to the previous question;
- measuring a neural response of the examinee associated with the examinee's response to the cue of the attestation affirmation; and
- comparing neural responses associated with the plurality of questions and the visual cue of the affirmation attestation with the baseline neural responses to determine if the examinee at least one of conducted deception in response to a question or malingered in response to a question.

* * * * *